United States Patent [19]
Buese et al.

[11] Patent Number: 5,247,116
[45] Date of Patent: Sep. 21, 1993

[54] ACID-CATALYZED PROCESS FOR THE PRODUCTION OF CYCLOSILOXANES

[75] Inventors: Mark A. Buese, Upper Darby; Pao-Sun Chang, Philadelphia, both of Pa.

[73] Assignee: Temple University of the Commonwealth System of Higher Education, Philadelphia, Pa.

[21] Appl. No.: 911,849

[22] Filed: Jul. 10, 1992

[51] Int. Cl.$^5$ .................................................. C07F 7/08
[52] U.S. Cl. ..................................... 556/460; 556/461
[58] Field of Search .............................. 556/460, 461

[56] References Cited

U.S. PATENT DOCUMENTS

| | | |
|---|---|---|
| 2,439,856 | 4/1948 | McGregor et al. .................. 556/460 |
| 2,860,152 | 11/1958 | Fletcher .............................. 556/460 |
| 3,222,320 | 12/1965 | Wolf ............................... 556/460 X |
| 3,714,213 | 1/1973 | Miller et al. . |
| 3,989,733 | 11/1976 | Okamoto et al. . |
| 4,113,760 | 9/1978 | Frey et al. ....................... 556/460 X |
| 4,197,251 | 4/1980 | Hirakawa et al. . |
| 4,276,425 | 6/1991 | Burkhardt et al. . |
| 4,895,967 | 1/1991 | Crivello et al. . |
| 5,068,383 | 11/1991 | Bourgoin et al. . |

FOREIGN PATENT DOCUMENTS 565276 10/1958 Canada .
585296 10/1959 Canada .

OTHER PUBLICATIONS

Hunter et al., *J. Amer. Chem. Soc.* 68, 667 (1946).
Chem. Abs. 87-118455(b) abstracting Japanese Patent Application 52/69500 (1977); and Crivello et al., *Chemistry of Materials* 1(4) 445 (1989).

*Primary Examiner*—Paul F. Shaver
*Attorney, Agent, or Firm*—Seidel, Gonda, Lavorgna & Monaco

[57] ABSTRACT

Cyclosiloxanes are produced by the acid-catalyzed redistribution of siloxane bonds in polysiloxane fluids at a temperature of about 20–200° C. Little catalyst and no water or solvent is required. Cyclosiloxane product mixtures contain $\leq 1$ wt. % cyclosiloxane species having more than 18 silicon-oxygen bonds, and $\leq 0.5$ wt. % cyclosiloxanes having 6 or fewer silicon-oxygen bonds, based upon the weight of the product mixture. The process may be carried out in continuous fashion where redistribution is carried out simultaneously with the stripping of cyclics from the equilibration mixture.

26 Claims, No Drawings

ACID-CATALYZED PROCESS FOR THE PRODUCTION OF CYCLOSILOXANES

FIELD OF THE INVENTION

The invention relates to the production of cyclosiloxanes, particularly the production of cyclosiloxanes from cyclic or linear polydimethylsiloxane or methylhydrogensiloxane fluids.

BACKGROUND OF THE INVENTION

Cyclosiloxane mixtures have been isolated from the hydrolysis of mixtures of dimethyldichlorosilane and methyldichlorosilane under dilute solution conditions (Heimberger et al., Plaste Kautsch. 25(7), 386 (1978)). This process typically results in the formation of linear oligomers and branched and bicyclic oligomers, due to competitive Si—H bond hydrolysis. The process does not permit the isolation of any particular component in high yield.

Cyclosiloxane mixtures have also been prepared by the dilute solution equilibration of siloxanes. According to the equilibration mechanism, two or more types of siloxane units undergo disproportionation to the extent that placements of siloxane units is completely random within all cyclic and linear species. The result is an "equilibrated" fluid. If linear fluids are used as the source of the cyclics, low molecular linear oligomers are also produced. Such linear oligomers can be detrimental to many applications for these cyclic oligomers. The isolation of cyclic oligomers in a 93% yield by depropagation has been described for dimethylsiloxanes using sodium hydroxide as a catalyst at 240° C. (Hunter et al., J. Amer. Chem. Soc. 68, 667 (1946)). Base catalysts may not be used with methylhydrogensiloxanes because of explosion hazards.

U.S. Pat. No. 2,860,152 and Canadian Patent 565,276 describe a method for producing cyclic diorganopolysiloxanes by heating a mixture of starting siloxanes in an inert solvent in an amount of at least 20% by weight based upon the weight of the siloxane, in the presence of an alkaline catalyst. More recently, U.S. Pat. No. 4,197,251 discloses the production of octamethylcyclotetrasiloxane by reacting dimethylsiloxane in the presence of an alkaline catalyst and inert solvent, while distilling cyclic dimethylsiloxanes.

U.S. Pat. No. 3,989,733 discloses production of cyclic polydiorganosiloxanes, particularly cyclic trisiloxanes, by thermal cracking and rectification over a hydroxide or carbonate of an alkali metal.

U.S. Pat. No. 2,439,856 and Canadian Patent 585,295 disclose the preparation of cyclic polymers of dimethyl silicone by hydrolyzing dimethyldiethoxysilicane in a 1:1 ratio with ethanol, in the presence of preferably an acid catalyst. The process results in cyclic polymers having up to thirteen silicon atoms.

U.S. Pat. No. 5,068,383 describes the catalyzed redistribution of monodispersed chloride and terminated polyorganosiloxane polymers. Acid clays may be utilized as the catalyst. Where cyclosiloxanes are produced, the reaction is run in the presence of stoichiometric or excess water in relation to the number of moles of starting chlorosiloxane to be redistributed.

U.S. Pat. No. 4,276,425 describes preparing cyclic dimethylpolysiloxanes by heating a mixture containing linear or branched organopolysiloxanes consisting of at least 50 mol% dimethylsiloxane units and aqueous $H_2SO_4$. A very large amount of the aqueous catalyst is used, 0.4–1.5 liter per kilogram of organopolysiloxane reactant.

Cyclosiloxanes which contain methylhydrogen siloxy groups have been prepared by depropagating fluids at high temperature on supported inorganic catalysts such as acid clays at 298° C. with 73% yield (U.S. Pat. No. 3,714,213); with acid clay catalyst and large quantities of water at 130° C. with 61% yield (Japan Kokai and published Patent Application JP 52/69500 (1977)); and with sulfuric acid clays, sulfuric acid impregnated molecular sieves or acidic zeolites at temperatures in excess of 300° C., 400° C., and 500° C., respectively under vacuum with a maximum of 86% yield (Crivello et al., Chemistry of Materials 1(4) 445 (1989); Crivello et al., U.S. Pat. No. 4,895,967). Large quantities of catalysts, often whose mass exceeds that of the siloxane reagents, are typically used. These processes are more efficient when the proportion of methylhydrogensiloxy units is high. The remaining reagents in the reaction mixture likely form a network residue due to radical cross-linking reactions which are known to occur readily at high temperatures, or due to Si—H hydrolysis and condensation reactions in the presence of water. Thus these methods do not readily permit continuous operation. The product that results generally has rings with 6 to 20 Si—O bonds with rings of 6 Si—O bonds predominating at high temperature. Six member ring siloxanes are strained and may not be used under many conditions where larger rings are stable. Except in the case of the acid zeolites, catalyst deactivation and contamination by sulfides is observed. Sulfide contamination is detrimental to subsequent hydrosilation reactions using transition metal catalysts. This is unfortunate, since transition metal catalyzed hydrosilation is one of the more important potential uses of cyclics mixtures.

SUMMARY OF THE INVENTION

The present invention is an improved process for the production of cyclosiloxanes from other cyclic siloxanes and/or linear siloxanes. Little catalyst is employed. No solvent and preferably no water are added. The invention is particularly useful for the preparation of cyclosiloxanes from cyclic and/or linear polydimethylsiloxane fluid and cyclic and/or linear methylhydrogensiloxane fluid.

It is accordingly one object of the invention to prepare cyclosiloxanes which have two or more disubstituted siloxy groups in the backbone of the cyclic siloxane, particularly cyclosiloxanes which contain dimethylsiloxy and methylhydrogen siloxy groups.

It is another object of the invention to provide for the isolation of desired cyclosiloxanes in high yield through recycling of an equilibrating reaction mixture of siloxane reactants.

It is an object of the invention to provide for the production of cyclosiloxane mixtures essentially free of linear oligomers.

It is a further object of the invention to provide product mixtures which essentially contain only strain-free cyclosiloxanes, that is, cyclosiloxanes containing at least 8 Si—O bonds. It is an object to provide cyclosiloxanes essentially free of rings which contain more than 18 Si—O bonds.

It is an object of the invention to provide a process for the production of cyclosiloxanes in the absence of added solvent, and with little or no water.

These and other objects of the invention will be apparent from the following description.

A process for producing cyclosiloxanes is provided. A reaction mixture is formed by contacting at least one siloxane selected from the group consisting of formula (I) and (II), or random or block copolymer of two or more different siloxanes according to formula (I),

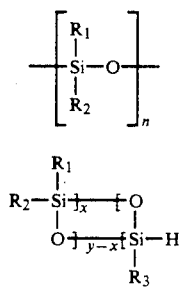

$$\left[ \begin{array}{c} R_1 \\ | \\ Si-O \\ | \\ R_2 \end{array} \right]_n \quad \text{I}$$

$$\begin{array}{c} R_1 \\ | \\ R_2-Si\!-\!\!\left[\phantom{x}\right]_x\!\!-\!\!O \\ | \phantom{xxx} | \\ O\!-\!\!\left[\phantom{y-x}\right]\!Si-H \\ \phantom{xxxxx} | \\ \phantom{xxxxx} R_3 \end{array} \quad \text{II}$$

wherein n is from 20 to 1,000,000, each $R_1$, $R_2$ and $R_3$ are independently selected from the group consisting of hydrogen, methyl, ethyl, propyl, vinyl, allyl, aryl, 3-hydroxypropyl, 3-chloropropyl and 3,3,3-trifluoropropyl, y is from 3 to 30, and x is from zero to y, with a strong acid catalyst in the absence of added solvent. The acid catalyst comprises no more than about 1% by weight of the siloxane reactants. A product mixture comprising volatile cyclosiloxanes is stripped from the reaction mixture.

In preferred embodiments of the invention, $R_1$, $R_2$ and $R_3$ are selected from hydrogen and methyl, or each of $R_1$, $R_2$ and $R_3$ is methyl. In another preferred embodiment y is from 4 to 14, more preferably from 4 to 9.

The acid-catalyzed equilibration of the siloxane reactants and stripping of the volatile cyclosiloxane products from the reaction mixture may take place in the same or different vessels. According to one embodiment, one or more siloxane reactants as defined above are charged to a first vessel in contact with a strong acid catalyst in the absence of added solvent and added water to form an equilibrating fluid reaction mixture comprising the siloxane reactant(s) and cyclosiloxanes. The acid catalyst is present in an amount of not more than about 1% by weight of the reaction mixture. At least a portion of the reaction mixture is transferred from the first vessel to a second vessel wherein volatile cyclosiloxanes are stripped therefrom and collected in a third vessel. The volatile cyclosiloxanes stripped from the reaction mixture comprise no more than about 1 wt. % cyclosiloxanes containing greater than 18 silicon-oxygen bonds, and no more than about 0.5 wt. % cyclosiloxanes containing 6 or fewer silicon-oxygen bonds, based upon the weight of the cyclosiloxanes. The stripped contents of the second vessel are recycled back to the first vessel. In this manner, the nonvolatile components of the reaction mixture are recycled to the first vessel.

According to a continuous mode of production, the reaction mixture is continuously or intermittently transferred from the first to the second vessel, volatile cyclosiloxanes are continuously or intermittently stripped from the reaction mixture in the second vessel and collected in a third vessel, and the stripped contents of the second vessel are continuously or intermittently recycled to the first vessel.

DETAILED DESCRIPTION OF THE INVENTION

Mixtures of cyclosiloxanes having ring sizes of primarily from 8 to 18 silicon-oxygen bonds are prepared in high yield from cyclosiloxanes of other ring sizes, and/or from linear siloxanes. In particular, cyclosiloxanes of the indicated ring sizes are prepared from cyclic and/or linear polydimethylsiloxane fluids, and from cyclic and/or linear methylhydrogensiloxane fluids. The process occurs by the acid-catalyzed redistribution of siloxane bonds.

The process relies on the establishment of a liquid phase equilibration reaction in which mixtures of cyclic and/or linear siloxanes (inclusive of polysiloxanes) are reacted in the presence of a strong acid catalyst to form a ring-chain equilibrium resulting in an equilibration mixture of linear siloxanes and the desired cyclosiloxanes. The equilibrium is constantly driven to the formation of cyclosiloxanes by removal of volatile cyclosiloxanes. Removal may be carried out batchwise, intermittently or continuously. Since the cyclosiloxanes are volatile, they may be conveniently separated from the equilibration fluid by stripping. By "stripping" is of course meant the removal of relatively volatile components of a liquid mixture such as by evaporation, distillation or passage of air or other gas through the mixture. If a nonvolatile catalyst is employed for the equilibration, the cyclosiloxane mixture can be used without any further purification as an intermediated in any one of a number of synthetic processes. Individual cyclosiloxanes can be isolated in very high overall yield via fractional distillation of the cyclosiloxane mixture. Such methods of fractional distillation are known to those skilled in the art. The residual cyclosiloxanes after the volatile cyclosiloxanes have been stripped out may be returned to the original equilibration mixture since both linear and cyclic siloxane fluids are reagents in the process. Specific desirable cyclosiloxanes which may be isolated in very high yield from the cyclosiloxane mixtures include, for example, heptamethylcyclotetrasiloxane, and mixed isomers of hexamethylcyclotetrasiloxane.

Cyclosiloxanes, particularly those which have dimethylsiloxy groups and methylhydrogensiloxy groups, may be produced in a controlled and efficient manner from one or more linear or cyclic siloxanes according to formula I or II, above. The linear or cyclic siloxane starting material used in the practice of the invention may be present in more or less pure form. More generally, the reactant will comprise a mixture of two or more siloxanes. The reactant may also comprise one or more random or block copolymers, inclusive of terpolymers and higher polymers also, of the formula I siloxanes. In such copolymers, the meaning of $R_1$ (and/or $R_2$) will of course vary to form the different monomer units comprising the copolymer.

The redistribution of silicon-oxygen bonds in the siloxane reactant is achieved by acid catalysis. Unlike base catalysts, acid catalysts may be used with methylhydrogensiloxanes without explosion hazard. Unlike prior art catalyzed processes of cyclosiloxane production by siloxane equilibration, a relatively small amount of catalyst mass is employed, not more than about 1 wt. % of the siloxane reactant.

The catalyst may comprise any strong acid. By "strong acid" is meant an acid which dissociates essentially completely in aqueous solution. Generally, the strong acids having utility in the practice of the present invention will have a $pK_a$ of at least as low as about $-4$. Acids useful as catalysts in the practice of the present invention include, in particular, trifluoromethanesulfonic acid, hydroidic acid, perchloric acid, $HBF_4$, $HBCl_4$, $HPCl_6$, $HPF_6$, $HSbCl_6$ and $HSbF_6$. Perchloric acid may be less useful as it could oxidize Si—H groups. Acids of less strength, such as sulfuric, phosphoric or even hydrochloric acid may be used provided the reactant residence time with the catalyst is sufficiently long. Aromatic acids may also be utilized, in particular aromatic sulonic acids such as any of the isomers of mono-substituted and disubstituted aromatic sulfonic acids, particularly the 2,4- and 2,6-disubstituted acids. Useful aromatic acids include, for example, benzenesulfonic, toluenesulfonic, nitrobenzenesulfonic, dinitrobenzenesulfonic, fluorobenzenesulfonic, difluorobenzenesulfonic, nitrotrifluoromethylbenzenesulfonic, trifluoromethylbenzenesulfonic, pentafluorobenzenesulfonic and benzenedisulfonic acids. By "aromatic sulfonic acid" is meant to include both substituted and unsubstituted aromatic sulfonic acids.

The reaction time may vary over a range. Typically, equilibration occurs in about one hour, starting from two homopolymer fluids with trifluoromethane sulfonic acid as the catalyst. Where separate equilibration and stripping vessels are employed, equilibrium is reestablished by depropagation to cyclic species in just a few minutes. The actual rate of equilibration depends on the nature and amount of catalyst utilized. Stripping is the rate limiting step in the process. The rate of stripping depends on the rate of introduction of the fluid into the stripper, the pressure and temperature in the stripper, the flow rate of any gas purge utilized, the fluid level and surface area of the stripper vessel. The stripper may be optionally packed with beads or turnings to increase the surface area.

The process produces cyclosiloxane mixtures which contain, on a weight percentage basis, no more than about 0.5% cyclic species containing 6 or fewer silicon oxygen bonds, and no more than about 1% cyclic species containing more than 18 silicon-oxygen bonds. Six-membered ring siloxanes are strained. They are more prone to ring-opening polymerization than unstrained rings. When they do polymerize, heat is generated and a relatively large shrinkage occurs. When unstrained rings are polymerized, no heat is generated and the shrinkage in the system is low. Six-membered rings are highly undesirable for end uses where ring-opening processes must be avoided, or end uses that require that no heat and little shrinkage be involved in polymerization. The present invention provides a method for producing strain-free cyclosiloxanes which can be used in such situations.

The proportion of the various cyclosiloxanes forming the product mixture can be varied by controlling the proportion of the reactants, and by controlling the temperature and pressure. In particular, the distribution of cyclic siloxanes may be altered by manipulating the temperature and pressure within the equilibration reaction zone. Where more than one reactant is employed the reactant ratio may vary over a wide range. For example, in one preferred embodiment wherein the reactants are polydimethylsiloxane and polymethylhydrogensiloxane, the ratio of the reactants may range from 100:0 to 0:100.

The proportion of eight-membered rings will increase with decreasing temperature and increasing pressure. Conversely the proportion of eighteen-membered rings will be highest at the highest temperature and lowest pressure. In all cases, the eight-member ring will be in the largest amount followed by the ten-, twelve-, fourteen-, sixteen- and eighteen-member rings. The eight-member ring will exceed forty percent of the mixture in all cases.

The proportion of cyclics with a given number of Si—H units will depend upon the proportion of the various siloxane units charged in the mixture. For example, if one desires the average cyclic tetramer to have two Si—H groups, the mole fraction of dimethylsiloxane units and methylhydrogen siloxane units should be approximately 0.5 and 0.5, respectively. If the cyclic tetramer with a single Si—H is desired, the ratio of dimethylsiloxane to methylhydrogensiloxane units should be 3 to 1 in the initially charged mixture.

The temperature and pressure of the reaction are directly related and can be varied over a wide range. The temperature may advantageously vary from about 20° C. to about 200° C. The equilibration reaction proceeds at room temperature. The temperature may be increased and reduced within these ranges in alternative cycles of stripping and equilibration until no further cyclics may be collected. Thus, the process of the invention employs temperatures substantially lower than prior art cyclosiloxane producing methods, which typically use temperatures in excess of 200° C. The pressure may vary from about 0.001 to about 100 mm of mercury. Preferably the temperature ranges from about 70° to about 140° C. The pressure preferably ranges from about 1 to about 50 mm Hg.

In the prior art, siloxane cracking for the production of cyclosiloxanes is typically carried out in the presence of a large amount of solvent. The acid-catalyzed equilibration reaction described herein is carried out in the absence of any added solvent, i.e. no solvent is introduced apart from the reactants themselves, which of course may function as mutual solvents. Thus, the need to separate the cyclosiloxane products from large amounts of solvent is obviated, along with the attendant expense.

The equilibrating fluid is cloudy in appearance, which may be due to small amounts of water and acid which have phase separated. Upon stripping, the fluid becomes clear. Exposure to the atmosphere results in the reappearance of cloudiness within seconds when stirred. Quantities of water which would result in gross phase separation would probably be detrimental to the rate of the process. The process is therefore preferably carried out without adding water to the system. This obviates the need to separate water from the cyclosiloxane product. Large amounts of water are further undesirable since this can lead to Si—H bond hydrolysis and condensation, resulting in a cross-linked network residue and gellation. If water is added in the reaction mixture, it should be held to no more than about 1%, although the actual upper limit in any particular circumstance will depend upon the acid concentration of the equilibrating mixture.

While water is preferably not actively added to the system, this is not to say that precautions are taken to dry the equilibrating fluids and catalysts. We have found that the system works best with fluids which have equilibrated in the presence of air which is not dry, but with no water added directly to the system. Thus, the preferred practice is to add no water to the system, but to take no precaution to keep atmospheric moisture from diffusing into the mixture. Thus, by "without added water" or "no water is added" is meant that the practice of the invention is undertaken without the purposeful addition of liquid water to the reaction mixture, but that no precautions are necessarily taken to prevent the diffusion of atmospheric moisture into the mixture.

The equilibration reaction and the cyclosiloxane stripping may be carried out in the same or different vessels. The construction and operation of devices suitable for these purposes are well known to those skilled in the art.

According to a one-pot embodiment, the reactant or reactants in the form of a siloxane fluid are combined with the strong acid catalyst and stirred. The volatile cyclosiloxanes are continuously stripped from the reaction mixture under vacuum, condensed and collected. As the volatile cyclosiloxanes are stripped from the fluid reaction mixture, the equilibrium shifts to favor the generation of more product. Stripping may be induced to occur over a broad temperature range, and is a function of both temperature and pressure.

More preferably, the equilibration reaction and stripping of cyclosiloxanes is carried out in two different vessels, with the vessel contents being mechanically transferred between them. According to one such two-vessel embodiment, fluid reactants are charged to a vessel and stirred in the presence of catalyst. The equilibrated fluid is removed and passed to a second vessel where stripping takes place, such as through a heated (e.g. 125° C.) stripping column. The volatile cyclics are condensed at the column top and collected, while the non-volatile linear portion of the fluid is drained from the column bottom and recycled to the equilibration vessel. Recycle of the fluid continues until no further cyclosiloxanes may be collected. While the practice of the invention is illustrated using a conventional stripping column, any device suitable temperature controlled device for the vaporization of volatile cyclosiloxanes may be substituted.

The process may be carried out batchwise, or in semi-continuous or continuous fashion. Reactants may be continuously or intermittently fed to a reaction zone where they are exposed to the catalyst, and volatile cyclosiloxanes are continuously or intermittently stripped from the equilibrating reaction mixture.

The nature and volatility of the catalyst may be important in determining the number of vessels should be employed. More than one vessel generally should be employed when the catalyst is volatile. This is because a quenching agent may be required, which will be contained in a separate cyclosiloxane receiving vessel. The quenching agent is advantageously a solid base which is insoluble in the cyclosiloxane mixture and easily filtered from that mixture. Suitable quenching agents include, for example, MgO; non-nucleophilic bases such as CaO, Ca(OH)$_2$, Mg(OH)$_2$, BaO, Ba(OH)$_2$, Li$_2$O and Li(OH)$_2$; and various amines. MgO is preferred. The quenching agent is used in an amount sufficient to inactivate any volatile catalytic species which may be carried with the cyclosiloxanes stripped from the equilibration mixture. The cyclosiloxanes may be separated from the insoluble base by the simple expedient of filtration.

The size of the linear polymer in equilibrium with the cyclics affects the composition of ring sizes. The concentration of a given cyclic is [cyclic x-mer]$=K_x p^x$ where $K_x$ is the equilibrium concentration for a cyclic in equilibrium with infinitely high molecular weight linear polymer. The quantity p is a probability term which describes the average size of the polymer which is in equilibrium with the cyclic where the average number of repeating units in the linear polymers is equal to $1/(1-p)$.

A nonvolatile disloxane may be optionally incorporated into the equilibration mixture to control the proportion of the different size cyclosiloxane rings produced. The disiloxane can be put in the mixture to keep the average ring size low, decrease the p value, and therefore increase the proportion of tetramer to pentamer to hexamer, etc.

Non-volatile disiloxanes may also be included for the purpose of reducing the viscosity of very high molecular weight siloxane fluids used as the reactant fluid, without introduction of volatile linear siloxanes. Non-volatile disiloxanes may be added to the equilibration mixture if the molecular weight of the reactant linear fluid is low. In this manner, the stripping of low molecular weight linear siloxanes along with the cyclosiloxanes is prevented. Alternatively, the stripping of linear oligomers can be avoided by keeping the equilibrated fluid viscosity high.

Inclusion of non-volatile disiloxanes in the equilibration mixture is also useful wherein cross-linked silicone rubbers are used as the reactant. Such rubbers may be used as the source of dimethylsiloxane units. In this manner, the present invention may be used as a process for the recycling of siloxane rubbers.

The amount of disiloxane added depends on the viscosity of the fluid used as the source of siloxane units. If the average molecular weight of the fluid is very high, an appropriate level of disiloxane may be found by slowly adding the disiloxane to the equilibrated fluid until the desired viscosity is achieved. If the viscosity of the fluid used is very low, it is desirable to add a non-volatile disiloxane to keep the proportion of very low molecular weight linear species with two volatile end groups low. Hence, for a fluid with an average of fifty repeating units, the addition of eight mole percent of disiloxane would reduce the proportion of volatile low molecular weight linears to only four percent of that in the absence of the disiloxane.

Low molecular weight linears are not a desirable component of the stripped cyclic mixture. The weight fraction of the small linears is inversely proportional to the average molecular weight of the linears. Therefore if the viscosity of the fluid remains above a certain level, the proportion of small linears will be acceptably low. The fluid viscosity can be kept high by adding fresh reagent equilibrated fluid when the original fluid has about 85-90% of its weight lost as cyclics. This is the least expensive way of maintaining high viscosity. If this fluid is always a linear polymer, a limit to the number of times a given fluid may be used as the source of catalyst would occur. Addition of the polymer fluid would constantly increase the number of end groups in the equilibrated fluid and, therefore increase the proportion of small linears. In a process where one or two desired cyclics are recovered from the cyclic mixture, the undesired cyclics could be returned to the equilibrating fluid. The addition of these cyclics or other cyclics to the depleted fluid would increase the molecular weight without adding end groups. The lifetime of the fluid would be significantly extended.

Non-volatile disiloxanes useful for the foregoing purposes include compounds of formula III

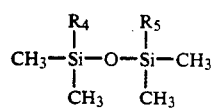

wherein $R_4$ and $R_5$ are independently selected from the group consisting of $C_6$ to $C_{24}$ straight and branched chain alkyl, preferably $C_8$ to $C_{18}$ straight- and branched-chain alkyl.

The yield of cyclosiloxane according to the process of the invention may in principle be quantitative due to the recycling of the equilibrating fluid. If one particular cyclosiloxane species is desired, it may be isolate from the cyclic product mixture by conventional techniques, e.g., fractional distillation, and the remainder of the cyclic mixture returned to the equilibrating mixture.

The practice of the invention is illustrated by the following non-limiting examples.

EXAMPLE 1

A 200 mL round bottle flask was charged with 117.5 g of polydimethylsiloxane and 32.5 g of polymethylhydrosiloxane which contained a ratio of dimethylsiloxy to methylsiloxy units of 3:1. Trifluoromethanesulfonic acid (0.15 g, 0.1% by weight) of reactants was added to the mixture which was then stirred at room temperature for 1 hour. The formation of cyclosiloxanes was indicated by a gas chromatographic analysis.

Mixed cyclosiloxanes were separated from the equilibrated siloxane fluid as follows. The siloxane fluid from the equilibrating flask was drawn into the top of a column (2.0 cm×63 cm) and allowed to pass therethrough. The column was heated at 125° C. under vacuum (2 mm Hg). The cyclosiloxanes were collected in a receiving flask which contained 0.8 g of MgO a cooled with a dry ice isopropanol bath. The non-volatile linear portion was drained from the column bottom column into another receiving flask. The linear fluid was then transferred back into the equilibrating flask and reintroduced into the stripping column. The rate at which the fluid was introduced into the column was controlled by a valve at the column top. The rate at which the fluid exited the column was controlled by a valve at the column bottom. The valves were set manually such that the rate at which the cyclic mixture dropped into the receiving flask was perceived to be the maximum. Periodically, the small contents of a trap between the condenser and the vacuum pump was returned to the equilibrating flask. The fluid was recycled until little additional cyclosiloxanes could be isolated. This occurred when the quantity of fluid was not sufficient to maintain equilibrium in the column with the volatile cyclosiloxanes. A total of 132.8 g of cyclosiloxanes (88.5% yield by weight) was obtained. The mixture contained 29.3% of heptamethylcyclotetrasiloxane, which is the cyclic which has exactly the proportion of dimethylsiloxy to methylhydrogensiloxy groups as was charged in the equilibrating fluid. The progress of the process is shown in Table 1.

TABLE 1

| No. of pass through column | Wt. of equilibrated fluid (grams) | Wt. of cyclics obtained (grams) | isolation yield of cyclics (wt. %) | Wt. of stripped fluid (grams) |
|---|---|---|---|---|
| 1 | 150 | 4.3 | 2.8 | 145.7 |
| 2 | 145.7 | 10.92 | 7.5 | 134.1 |
| 3 | 134.1 | 10.78 | 8.0 | 123.3 |
| 4 | 123.3 | 8.6 | 6.5 | 114.5 |
| 5 | 114.5 | 6.9 | 6.0 | 107.6 |
| 6 | 107.6 | 9.3 | 8.6 | 98.3 |
| 7 | 98.3 | 6.8 | 6.9 | 91.5 |
| 8 | 91.5 | 5.1 | 5.5 | 86.4 |
| 9 | 86.4 | 6.7 | 7.9 | 79.7 |
| 10 | 79.7 | 5.8 | 7.3 | 73.9 |
| 11 | 73.9 | 5.0 | 6.7 | 67.2 |
| 12 | 67.2 | 5.45 | 8.1 | 61.7 |
| 13 | 61.7 | 4.6 | 7.4 | 57.2 |
| 14 | 57.2 | 4.0 | 7.0 | 53.2 |
| 15 | 53.2 | 4.2 | 7.9 | 49.0 |
| 16 | 49.0 | 4.3 | 8.7 | 44.6 |
| 17 | 44.6 | 3.8 | 8.5 | 40.8 |
| 18 | 40.8 | 3.4 | 8.2 | 37.4 |
| 19 | 37.4 | 3.1 | 8.3 | 34.3 |
| 20 | 34.3 | 2.4 | 7.0 | 32.0 |
| 21 | 32.0 | 2.0 | 6.7 | 30.0 |
| 22 | 30.0 | 2.0 | 6.7 | 28.0 |
| 23 | 28.0 | 2.2 | 8.1 | 25.8 |
| 24 | 25.8 | 2.1 | 7.9 | 23.8 |
| 25 | 23.8 | 1.6 | 6.6 | 22.2 |
| 26 | 22.2 | 1.5 | 6.7 | 20.7 |
| 27 | 20.7 | 1.3 | 6.2 | 19.4 |
| 28 | 19.4 | 1.2 | 5.9 | 18.2 |
| 29 | 18.2 | 1.0 | 5.5 | 17.2 |

EXAMPLE 2

From a column of larger dimensions (3.5 cm×98 cm), an equilibrated fluid which contained 3,000 grams of polydimethylsiloxane, 1,000 grams of polymethylhydrogensiloxane, and 2 mL of trifluoromethanesulfonic acid was stripped of cyclosiloxanes as follows. The fluid from an equilibrating flask was passed through the column at 140° C. and 2 mm Hg pressure, at a rate such that 1 L of mixed cyclosiloxanes was collected in an 8 hour period. The stripping was carried out continuously until 3,800 grams (92%) of the original fluid was converted into mixed cyclosiloxanes. The equilibrating fluid was then charged with an additional 750 grams of polydimethylsiloxane and 250 grams of polymethylhydrogensiloxane. Upon stripping of cyclosiloxanes, the equilibrating flask was reduced to 100% of its tare weight, indicating complete conversion of the second charge of fluid into cyclosiloxanes.

EXAMPLE 3

The following semicontinuous, one-pot process was carried out using a rotary evaporator rather than the stripper described above.

Into a 2000 mL round bottomed flask were placed 750 g of octamethylcyclotetrasiloxane, 150 g of polymethylhydrogensiloxane and 150 grams of polydimethylco-methylhydrogensiloxane with octyldimethylsiloxy end groups which remained from a previous isolation of cyclosiloxanes. The reaction mixture was stirred at room temperature until well dispersed. A 2 g portion of trifluoromethanesulfonic acid was added to the flask. The reaction mixture was kept at room temperature for two hours during which time the mixture became viscous and cloudy. The cyclic mixture was stripped from the reaction mixture using a rotary evaporator and a vacuum of approximately 15 mm Hg using a mechanical pump equipped with a trap cooled by liquid nitrogen.

The water bath was maintained at 85° C. and MgO was present in the receiving flask, which was cooled with a dry ice-isopropanol bath. After 30 minutes, the removal of cyclics was extremely slow and the stripping was stopped. The trap was removed and the liquid from the trap was returned to the equilibrating fluid. The flask was again placed on the rotary evaporator and the stripping continued until it again slowed considerably. By multiple repetitions of this stripping procedure a total of 950 grams of the cyclic mixture was obtained.

The present invention may be embodied in other specific forms without departing from the spirit or essential attributes thereof and, accordingly, reference should be made to the appended claims, rather than to the foregoing specification, as indicating the scope of the invention.

We claim:

1. A process for producing cyclosiloxanes comprising:
   (a) forming a reaction mixture by contacting
      at least one siloxane of formula I or II, or random or block copolymer of two or more different siloxanes according to formula I,

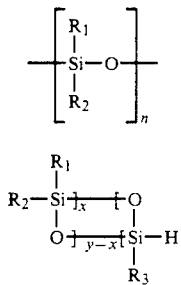

wherein
n is from 20 to 1,000,000,
each $R_1$, $R_2$ and $R_3$ are independently selected from the group consisting of hydrogen, methyl, ethyl, propyl, vinyl, allyl, aryl, 3-hydroxypropyl, 3-chloropropyl and 3,3,3-trifluoropropyl,
y is from 3 to 30, and
x is from zero to Y,
with a strong acid catalyst in the absence of an added solvent, said acid catalyst comprising no more than about 1% by weight of the siloxane reactants;
   (b) stripping a product mixture comprising volatile cyclosiloxanes from the reaction mixture.

2. A process according to claim 1 comprising forming the reaction mixture in a first vessel,
removing a portion of the reaction mixture continuously or intermittently from the first vessel to a second vessel,
stripping volatile cyclosiloxanes from the contents of the second vessel, and
continuously or intermittently recycling the stripped contents of the second vessel back to the first vessel.

3. A process according to claim 1 wherein y is from 4 to 14.

4. A process according to claim 1 wherein $R_1$, $R_2$ and $R_3$ are selected from the group consisting of hydrogen and methyl.

5. A process according to claim 4 wherein $R_1$, $R_2$ and $R_3$ are methyl.

6. A process according to claim 4 wherein the siloxane reactant comprises polydimethylsiloxane, polymethylhydrosiloxane, or mixture thereof.

7. A process according to claim 1 wherein the acid catalyst is selected from the group consisting of trifluoromethanesulfonic acid, hydroiodic acid, perchloric acid, $HBF_4$, $HBCl_4$, $HPF_6$, $HPCl_6$, $HSbCl_6$, $HSbF_6$ and aromatic sulfonic acids.

8. A process according to claim 1 wherein the acid catalyst has a $pK_a$ of at least as low as about $-4$.

9. A process according to claim 7 wherein the catalyst is trifluoromethanesulfonic acid.

10. A process according to claim 1 wherein the volatile cyclosiloxanes stripped from the reaction mixture contain no more than about 1 wt. % cyclosiloxanes containing more than 18 silicon-oxygen bonds, and no more than about 0.5 wt. % cyclosiloxanes containing six or fewer silicon-oxygen bonds.

11. A process according to claim 1 wherein the temperature is from about 20° to about 200° C.

12. A process according to claim 1 wherein the temperature is from about 70° to about 140° C.

13. A process according to claim 1 wherein the pressure in a vessel containing the reaction mixture is from about 0.00 to about 100 mm of mercury.

14. A process according to claim 13 wherein the pressure in a vessel containing the reaction mixture is from about 1 to about 50 mm of mercury.

15. A process according to claim 1 wherein one or more selected cyclosiloxanes are distilled from the cyclosiloxane product mixture, and the remainder of the product mixture following the distillation is recycled to the reaction mixture.

16. A process according to claim 1 wherein the reaction mixture includes one or more non-volatile disiloxanes.

17. A process according to claim 16 wherein the non-volatile disiloxane is selected from the group defined by formula III.

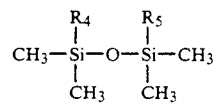

wherein
$R_4$ and $R_5$ are independently selected from the group consisting of $C_6$ to $C_{24}$ straight- and branched-chain alkyl.

18. A process according to claim 17 wherein $R_4$ and $R_5$ are selected from the group consisting of $C_8$ to $C_{18}$ straight- and branched-chain alkyl.

19. A process according to claim 1 wherein no water is added to the reaction mixture.

20. A process according to claim 1 wherein the cyclosiloxane product includes heptamethylcyclotetrasiloxane.

21. A process according to claim 1 wherein the cyclosiloxane product includes one or more isomers of hexamethylcyclotetrasiloxane.

22. A process for the production of a cyclosiloxane mixture containing no more than about 1 wt. % cyclosiloxanes containing greater than 18 silicon-oxygen bonds and no more than about 0.5 wt. % cyclosiloxanes containing 6 or fewer silicon-oxygen bonds, the process comprising:

(a) contacting in a first vessel
one or more siloxane reactants according to the formula I or II, or random or block copolymer of two or more different siloxanes according to formula I,

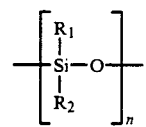

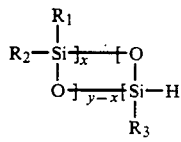

wherein n is from 20 to 1,000,000, each $R_1$, $R_2$ and $R_3$ is independently selected from the group consisting of hydrogen, methyl, ethyl, propyl, vinyl, alkyl, aryl, 3-hydroxypropyl, 3-chloropropyl and 3,3,3-trifluoropropyl, y is from 3 to 30, and x is from zero to Y, with a strong acid catalyst in the absence of added solvent and added water to form an equilibrating fluid reaction mixture comprising the siloxane reactants and cyclosiloxanes; said strong acid catalyst comprising no more than bout 1% by weight of the reaction mixture;

(b) transferring at least a portion of the reaction mixture to a second vessel wherein volatile cyclosiloxanes are stripped from the reaction mixture, said cyclosiloxanes comprising no more than about 1 wt. % cyclosiloxanes containing greater than 18 silicon-oxygen bonds, and no more than about 0.5 wt. % cyclosiloxanes containing 6 or fewer silicon-oxygen bonds, based upon the weight of the said cyclosiloxanes; and (c) recycling the stripped contents of the second vessel back to the first vessel.

23. A process according to claim 22 wherein $R_1$, $R_2$ and $R_3$ are selected from the group consisting of hydrogen and methyl.

24. A process according to claim 22 wherein the equilibrating fluid reaction mixture includes one or more non-volatile disiloxanes.

25. A process according to claim 22 wherein the reaction mixture is continuously or intermittently transferred from the first to the second vessel, volatile cyclosiloxanes are continuously or intermittently stripped from the reaction mixture in the second vessel, and the stripped contents of the second vessel are continuously or intermittently recycled to the first vessel.

26. A process according to claim 25 wherein the volatile cyclosiloxanes are collected in a third vessel containing a quenching agent for deactivating the catalyst.

* * * * *